United States Patent [19]

Mase et al.

[11] Patent Number: 4,798,693
[45] Date of Patent: Jan. 17, 1989

[54] METHOD OF MANUFACTURING AN ELECTROCHEMICAL DEVICE

[75] Inventors: Syunzo Mase, Ama; Shigeo Soejima, Nagoya, both of Japan

[73] Assignee: NGK Insulators, Ltd., Nagoya, Japan

[21] Appl. No.: 81,631

[22] Filed: Aug. 3, 1987

Related U.S. Application Data

[63] Continuation of Ser. No. 725,672, Apr. 22, 1985, abandoned.

[30] Foreign Application Priority Data

Apr. 26, 1984 [JP] Japan .................... 59-84677

[51] Int. Cl.$^4$ .......................................... G01N 27/46
[52] U.S. Cl. ................................... 264/44; 204/425; 204/426; 204/427; 264/61
[58] Field of Search ................ 204/1 S, 421–429; 264/61, 44; 65/59.22

[56] References Cited

U.S. PATENT DOCUMENTS

| | | | |
|---|---|---|---|
| 3,978,006 | 8/1976 | Topp et al. | 204/429 |
| 4,021,326 | 5/1977 | Pollner et al. | 204/429 |
| 4,304,652 | 12/1981 | Chiba et al. | 204/425 |
| 4,334,974 | 6/1982 | Muller et al. | 204/425 |
| 4,402,820 | 9/1983 | Sano et al. | 204/429 |
| 4,449,919 | 5/1984 | Takikawa et al. | 204/429 |
| 4,498,968 | 2/1985 | Yamada et al. | 204/425 |
| 4,502,939 | 3/1985 | Holfelder et al. | 264/61 |
| 4,505,806 | 3/1985 | Yamada | 204/426 |
| 4,505,807 | 3/1985 | Yamada | 204/429 |

FOREIGN PATENT DOCUMENTS 0064666 11/1982 European Pat. Off. .
2449887 9/1980 France .
2054868 2/1981 United Kingdom .

*Primary Examiner*—T. Tung
*Attorney, Agent, or Firm*—Parkhurst, Oliff & Berridge

[57] ABSTRACT

A method of manufacturing an electrochemical device having an electrochemical cell including a planar solid electrolyte body and at least two electrodes disposed in contact with the solid electrolyte body. The method comprising: forming a first unfired ceramic layer on one side of an unfired structure of the electrochemical cell, the first unfired ceramic layer being given a porous structure by firing thereof; forming a second unfired ceramic layer on the other side of the unfired structure of the electrochemical cell, the second unfired ceramic layer having substantially the same property of firing shrinkage as the first unfired ceramic layer; and co-firing the unfired structure of the electrochemical cell, the first and second unfired ceramic layers. The two unfired ceramic layers may be formed on opposite sides of an unfired structure of an electrochemical cell assembly which includes plural cells, for example, an oxygen pumping cell and an oxygen sensing cell. In this case, another unfired ceramic layer may be formed between the unfired structures of the two cells. The electrochemical device manufactured by the method does not have a unfavorable warpage that would arise due to difference in firing shrinkage between the layers.

10 Claims, 6 Drawing Sheets

METHOD OF MANUFACTURING AN ELECTROCHEMICAL DEVICE

This is a continuation of application Ser. No. 725,672, filed Apr. 22, 1985, now abandoned.

BACKGROUND OF THE INVENTION

The present invention relates in general to an electrochemical device and a method of manufacturing the same. More particularly, the invention is concerned with an improved method of producing an electrochemical device having a laminar structure which includes an electrochemical cell using a planar solid electrolyte body, and is also concerned with an electrochemical device produced by such an improved method.

There have been known various electrochemical devices using solid electrolyte, for example, oxygen sensors to detect the oxygen concentration of an exhaust gas emitted from internal combustion engines of automotive vehicles. The typical examples of such oxygen sensors include: an oxygen sensor which comprises a tubular body of oxygen-ion conductive solid electrolyte such as zirconia ceramics, and electrodes of platinum or the like provided on both inner and outer surfaces of the tubular solid electrolyte body, and which operates to determine the oxygen concentration according to the principle of an oxygen concentration cell; an oxygen sensor similar to the above, which incorporates a heater which enables the sensor to operate at a relatively low exhaust gas temperature; and a so-called "lean-burn" sensor suitable for detecting the oxygen concentration of an exhaust gas which is produced at lean air-fuel ratios, i.e., an exhaust gas having a larger oxygen content. Also known in the art are electrochemical sensing and pumping devices for detecting or controling hydrogen, nitrogen, carbon dioxide gas, etc.

In such electrochemical devices, solid electrolyte materials have been generally used in the form of a tubular body which has an elongate bore closed at its one end. In recent years, however, it has been attempted to replace the tubular solid electrolyte body with a solid electrolyte body of planar shape, as disclosed in U.S. Pat. No. 4,334,974, in view of relatively low productivity and high cost of manufacture of the solid electrolyte bodies of tubular shape, and from the standpoint of easy assembling of parts with the solid electrolyte body. When such planar solid electrolyte bodies are employed, suitable electrodes are disposed in contact with the surfaces of a layer or layers of solid electrolyte, and the electrolyte layers and other parts are assembled into a laminar structure constituting an electrochemical cell or cells.

In this type of electrochemical device wherein planar or plate-like layers of solid electrolyte are laminated, an electrically insulating porous protective layer of ceramics may be disposed on one side of a planar laminar electrochemical cell to protect a measuring electrode against direct exposure to an external measurement gas, or an electrically insulating layer may be interposed between the other side of the laminar electrochemical cell and a planar electrical heater to heat the cell (more precisely, its detecting portion adjacent the electrodes), in order to electrically insulate the electrical heater. In the case where such a porous protective or insulating layer is disposed on only one side of the electrochemical cell, however, the generally planar electrochemical device tends to warp or buckle due to a difference in shrinkage during firing between the solid electrolyte material of the cell and the ceramic material of the insulating layer. For example, the electrochemical device using such a protective or insulating layer may warp such that the protective or insulating layer is outwardly convex. Thus, the conventional electrochemical device of the type described above suffers a problem of warpage during manufacture.

SUMMARY OF THE INVENTION

The present invention was developed in view of the above-discussed background. It is accordingly an object of the invention to provide a method of manufacturing an electrochemical device, which prevents warpage of the device during manufacture. Another object of the invention is to provide a highly reliable and durable electrochemical device of generally planar laminar structure which has substantially no warpage, and in which a planar electrical heater is protected against deterioration and electrical leakage.

According to the present invention, there is provided a method of manufacturing an electrochemical device which has an electrochemical cell including a planar solid electrolyte body and at least two electrodes disposed in contact with the solid electrolyte body, the method comprising the steps of: forming a first unfired ceramic layer on one side of an unfired structure of the electrochemical cell, the first unfired ceramic layer being given a porous structure by firing thereof; forming a second unfired ceramic layer on the other side of the unfired structure of the electrochemical cell, the second unfired ceramic layer having substantially the same property of firing shrinkage as the first unfired ceramic layer; and co-firing the unfired structure of the electrochemical cell, and the first and second unfired ceramic layers.

In the instant method of the invention, the unfired planar solid electrolyte body is co-fired with the two unfired ceramic layers which are substantially identical in the property of firing shrinkage, and which are disposed on both sides of the unfired planar solid electrolyte body. In this arrangement, a stress that acts on one side of the unfired structure to cause warpage in one direction due to a difference in firing shrinkage between the unfired solid electrolyte body and one of the two unfired ceramic layers, counteracts or counterbalances a stress that acts on the other side of the unfired structure to cause warpage in the other direction due to a difference in firing shrinkage between the unfired solid electrolyte body and the other unfired ceramic layer. As a result, the occurrence of warpage or buckling of the planar electrochemical device as a whole is effectively avoided.

According to another aspect of the invention, there is provided a method of manufacturing an electrochemical device which has a planar electrochemical cell assembly which includes a plurality of electrochemical cells, each of the electrochemical cells including a planar solid electrolyte body and at least two electrodes disposed in contact with the solid electrolyte body, the method comprising: forming a first unfired ceramic layer on one side of an unfired structure of the planar electrochemical cell assembly, the first unfired ceramic layer being given a porous structure by firing thereof; forming a second unfired ceramic layer on the other side of the unfired structure of the electrochemical cell assembly, the second unfired ceramic layer having substantially the same property of firing shrinkage as the first unfired ceramic layer; and co-firing the unfired structure of the electrochemical cell assembly, and the first and second unfired ceramic layers.

According to one advantageous embodiment of the method of the invention described above, the electrochemical cell assembly includes a pumping cell and a sensing cell. The first unfired ceramic layer is formed so as to cover one side of an unfired structure of the pumping cell, while the second unfired ceramic layer is formed so as to cover one side of an unfired structure of the sensing cell remote from the unfired structure of the pumping cell. In this instance, a third unfired ceramic layer may be formed between the unfired structures of the pumping and sensing cells.

Moreover, the method of the present invention may be suitably practiced for manufacturing an electrochemical device of the following structure.

Namely, the instant method is suitable for producing an electrochemical device wherein two porous ceramic layers are disposed respectively on opposite sides of an electrochemical cell comprising a planar solid electrolyte body and at least two electrodes disposed in contact with the solid electrolyte body, and wherein at least one of the two porous ceramic layers serves as an electrically insulating layer, and a planar electrical heater to heat the solid electrolyte body is provided in contact with this electrical insulating layer. The electrical heater has a gas-tight ceramic outermost layer.

In the electrochemical device constructed as described above, the electrical heater provided to heat the solid electrolyte body assures stable and accurate sensing operations even while the temperature of a measurement gas is relatively low, for example, immediately after an engine is started the exhaust gas of which is detected. Further, the arrangement indicated above makes it possible to increase the durability of the electrical heater, prevent current leakage from the heater and warpage of the device, thus improving the operating reliability of the device. Stated more specifically, the gas-tight ceramic outermost layer of the electrical heater protects the heating element against exposure to the surrounding atmosphere, (i.e., measurement gas) in order to prevent scattering of metal components of the heating element at an elevated temperature, whereby the deterioration of the electrical heater is effectively restrained. Further, the gas-tight ceramic outermost layer protects the electrical heater against exposure to corrosive gases in the measurement gas, thereby increasing the durability of the heater. Moreover, the provision of the electrically insulating porous ceramic layer interposed between the electrochemical cell and the electrical heater provides a solution to the problem of cracks and flake-off or peel-off of the electrochemical device which would arise due to difference in thermal expansion between different layers of the device, and to the problem of current leakage from the electrical heater.

In one advantageous embodiment of the invention, a heating portion of the electrical heater is sandwiched between and in contact with the electrically insulating porous ceramic layer and the gas-tight ceramic outermost layer.

In accordance with another advantageous embodiment of the invention, the heating portion of the electrical heater is embedded in a porous ceramic structure. In this case, the porous ceramic structure may comprise the previously indicated electrically insulating porous ceramic layer.

In an alternative embodiment of the invention, the heating portion of the heater is embedded in a gas-tight ceramic structure. In this instance, the gas-tight porous structure may comprise the previously indicated gas-tight ceramic outermost layer.

According to a further aspect of the invention, there is provided an electrochemical device having a planar electrochemical cell assembly which includes a plurality of electrochemical cells, each of the electrochemical cells including a planar solid electrolyte body and at least two electrodes disposed in contact with the solid electrolyte body, the electrochemical device comprising two porous ceramic layers disposed on opposite sides of the planar electrochemical cell assembly, respectively, at least one of the two porous ceramic layers serving as an electrically insulating layer. The electrochemical device further comprises a planar electrical heater formed in contact with the electrically insulating layer. The planar electrical heater has a gas-tight ceramic outermost layer. The electrochemical cell assembly may include a pumping cell and a sensing cell. One of the two porous ceramic layers is disposed so as to cover one side of the pumping cell, while the other porous ceramic layer is disposed so as to cover one side of the sensing cell remote from the pumping cell. Another porous ceramic layer may be disposed between the pumping and sensing cells.

BRIEF DESCRIPTION OF THE DRAWING

The foregoing and other objects, features and advantages of the present invention will become more apparent from reading the following detailed description of the preferred embodiments of the invention in conjunction with the accompanying drawings, in which.

DETAILED DESCRIPTION OF THE PREFERRED EMBODIMENTS

Referring more particularly to the accompanying drawings, several arrangements embodying the concept of the present invention will be described in detail for purposes of illustration.

Figure 1:
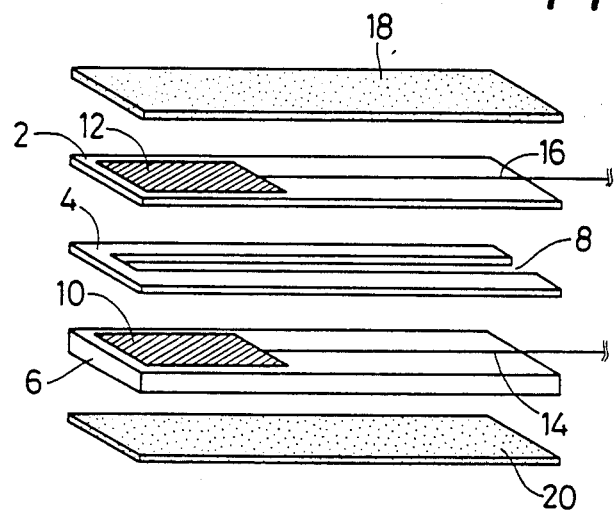
FIGS. 1 through 4 are exploded perspective views of different forms of a sensing element of an electrochemical device of the invention in the form of an oxygen sensor, respectively.

There is first shown in an exploded perspective view of FIG. 1 a sensing element in one example of an oxygen-concentration detector which is one embodiment of an electrochemical device of the invention. This sensing element of the oxygen-concentration detector or oxygen sensor includes a planar solid electrolyte layer 2 made of zirconia ceramics containing yttria, or the like, a planar spacer layer 4 and a planar support layer 6 which are made of the same solid electrolyte material as the solid electrolyte layer 2. These planar layers 2, 4 and 6 of solid electrolyte constitute a generally planar or sheet-like solid electrolyte body of laminar structure.

The spacer layer 4 sandwiched by the solid electrolyte layer 2 and the support layer 6 has an elongate recess 8 formed longitudinally thereof so as to serve as a reference-gas passage 8 in which a reference substance is introduced. A porous reference electrode 10 made of platinum, for example, is disposed on one surface of the support layer 6 so that the reference electrode 10 is exposed to the reference substance (reference gas) such as ambient air introduced in the reference-gas passage 8. On the outer surface of the solid electrolyte layer 2, there is disposed a porous measuring electrode 12 which is made of platinum, for example, so that the measuring electrode 12 is exposed to a measurement gas such as an exhaust gas from an engine of a vehicle.

The reference and measuring electrodes 10, 12 are provided with respective electrical leads 14, 16 which are electrically connected to a suitable external measuring device, so that an electric potential between the two electrodes 10, 12 is measured by the measuring device. More particularly stated, the external measuring device measures an electromotive force which is produced between the measuring electrode 12 exposed to the measurement gas, and the reference electrode 10 exposed to the reference gas (ambient air), due to a difference in oxygen concentration between the measurement gas and the reference gas.

The outer surface of the solid electrolyte layer 2 on which the measuring electrode 12 is disposed is covered by a porous ceramic layer 18. The surface of the support layer 6 opposite to the surface on which the reference electrode 10 is disposed, that is, the outer surface of the support layer 6, is covered with a ceramic layer 20 (porous ceramic layer in this case) made of a ceramic material which has substantially the same shrinkage characteristic during firing thereof, as that of the porous ceramic layer 18.

The sensing element of the electrochemical device constructed as described above, is manufactured in the following manner. First, unfired layers of the electrodes 12, 10 and electrical leads 16, 14 are formed, in a known screen-printing or similar process, on respective unfired green sheets of the solid electrolyte layer 2 and support layer 6. A paste of ceramic particles which will form the porous ceramic layers 18, 20 by firing, is applied by printing to the outer surfaces of the green sheets of the solid electrolyte layer 2 and support layer 6, before or after the green sheets of the layers 2, 6 and the green sheet of the spacer layer 4 have been superposed into an unfired laminar structure so that the spacer layer 4 is sandwiched by the layers 2 and 6. The laminar structure of the green sheets with the ceramic paste applied for formation of the porous ceramic layers 18, 20, is then co-fired in a known manner, whereby the sensing element of the electrochemical device in the form of an oxygen sensor is produced.

In the above-indicated method, the unfired ceramic layers 18, 20 having substantially the same property of firing shrinkage are formed on the opposite sides of the unfired laminar green-sheet structure of the generally planar solid electrolyte 2, 4, 6 which constitutes an electrochemical cell. In this arrangement, a stress that acts on one side of the unfired laminar structure to cause warpage in one direction due to a difference in firing shrinkage between the unfired solid electrolyte body 2, 4, 6 and one of the unfired ceramic layers 18, 20, counteracts or counterbalances a stress that acts on the other side of the unfired laminar structure to cause warpage in the other direction due to a difference in firing shrinkage between the unfired solid electrolyte body 2, 4, 6 and the other unfired ceramic layer 18, 20. As a result, the occurrence of warpage or buckling of the planar electrochemical cell as a whole is effectively restrained.

The ceramic layer 18 covering the outer surface of the solid electrolyte layer 2 on which the measuring electrode 12 is formed, should be of a porous structure so that the measuring electrode 12 is exposed to the measurement gas, such as an exhaust gas, through the porous structure of the ceramic layer 18. In other words, the porous ceramic layer 18 protects the measuring electrode 12 against direct contact with a flow of the measurement gas.

On the other hand, the ceramic layer 20 covering the outer surface of the support layer 6, is provided primarily for preventing the warpage of the laminar solid electrolyte body 2, 4, 6 due to the existence of the porous ceramic layer 18. The ceramic layer 20 may be either porous or gas-tight, but should however exhibit the firing shrinkage property which is substantially identical to that of the porous ceramic layer 18.

These two ceramic layers 18, 20 are preferably formed of a ceramic material the major component of which is alumina or spinel. However, the ceramic layers 18, 20 may be made of ceramics whose major component is borosilicate glass, mullite, steatite, forsterite, cordierite, or zircon. Since these ceramic materials have electrically insulating property, the ceramic layers 18, 20 may be suitably used for blocking current leakage from an electrical heater if a layer of the heater is disposed on the ceramic layer 18, 20.

The firing shrinkage properties of the ceramic layers 18, 20 may be adjusted as needed in a known manner. Generally, the ceramic material of the same chemical composition is used for both ceramic layers 18, 20, and the shrinkage property is determined by adjusting the particle size, and size distribution of the ceramic particles, and by adjusting an amount of a sintering agent to be added to the ceramic paste. The easiest method for giving the ceramic layers 18, 20 the same firing shrinkage property, is to use a paste of ceramic particles which is prepared in the same batch. The ceramic layers 18, 20 which are made of the ceramic material discussed above, are usually formed so that their porosity is held within an approximate range of 5-30%.

The solid electrolyte body 2, 4, 6 which forms a substantive part of the electrochemical cell may be made of beta-alumina, aluminum nitride, NASICON, $SrCeO_3$, solid solution of bismuth oxide-oxide of rare earth element, $La_{1-x}Ca_xYO_{3-\alpha}$, or the like, in place of the previously indicated zirconia ceramics.

Since the electrochemical cell is produced by means of concurrent firing of the unfired layers 2, 4, 6, 18 and 20 as previously described, it is preferred to co-fire the electrodes 10, 12 and and their electrical leads 14, 16 together with the unfired laminar structure of the layers 2, 4, 6, 18 and 20. In this instance, these electrodes and leads are preferably formed by printing, using as major components thereof elements of the platinum group including platinum, palladium, rhodium, iridium, ruthenium and osmium. The printed layers are finally fired to form the intended layers of electrodes and leads. In this connection, it is preferred to admix fine ceramic particles of zirconia, alumina, or a similar material with the above-indicated electrically conductive materials, for preventing flake-off and disconnection of the electrodes 10, 12 and leads 14, 16, (i.e., for increasing the adhesion of the electrodes and leads to the surfaces of the layers 2 and 6 during the firing process).

While one form of an electrochemical sensing element of an electrochemical device of the invention has been described with a certain degree of particularity in connection with the construction and method of manufacture, the invention is by no means limited to the precise disclosure of the above embodiment, but may be applied to other types of electrochemical devices, and other forms of the laminar electrochemical sensing element as illustrated in FIGS. 2 through 9. The constructions of the electrochemical sensing elements illustrated in these figures are improved in terms of freedom from current leakage from an electrical heater, operating reliability and durability, as well as in freedom from warpage due to firing shrinkage.

Figure 2:
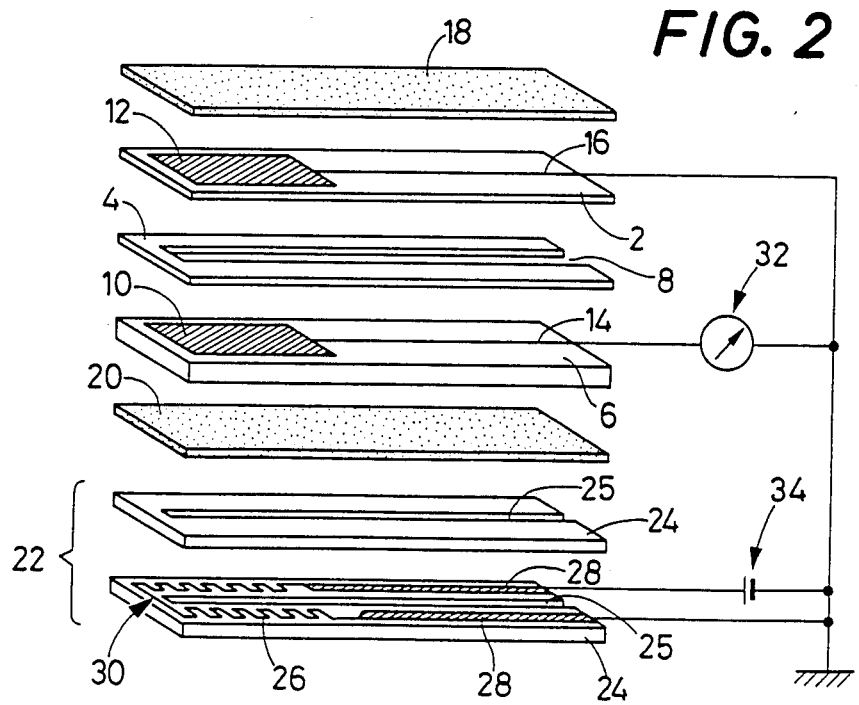

The oxygen sensing element shown in FIG. 2 further includes a planar electrical heater 22 which is disposed in contact with the porous ceramic layer 20 of the sensing element of FIG. 1. The electrical heater 22 comprises a pair of gas-tight ceramic layers 24, 24 each of which has an elongate slit 25 formed in the longitudinal direction, and further comprises a heating portion 30 which is sandwiched by the gas-tight ceramic layers 24, 24. In other words, the heating portion 30 is embedded in a gas-tight ceramic structure 24, 24. The heating portion 30 includes a heating element 26 and a pair of electrical leads 28. The material of the gas-tight ceramic layers 24, 24 is selected from known ceramic materials such as zirconia, alumina, mullite, spinel, titania, barium titanate and calcium zirconate. However, it is particularly preferred to use zirconia as a major component of the ceramics for these layers 24, 24.

The heating element 26 and leads 28, 28 of the heating portion 30 of the electrical heater 22 may be made of elements of the platinum group which includes platinum, palladium, rhodium, iridium, ruthenium and osmium, or of metals having a high melting point such as nickel, tantalum or tungsten, or alloys such as nichrome. Preferably, the heating element 26 and leads 28, 28 are made of a mixture of an element of the platinum group and ceramics such as zirconia, alumina or spinel. With the use of such a mixture, the adhesion of the heating element 26 and leads 28, 28 to the mating surfaces of the gas-tight ceramic layers 24, 24 is improved. The mixture of the above-indicated metal and ceramics (in the form of fine particles) is applied in a predetermined pattern on one of the gas-tight ceramic layers 24, 24, and co-fired together with the ceramic layers 24, 24, and with the solid electrolyte body 2, 4, 6 and the porous ceramic layers 18, 20, whereby the integral oxygen sensing element of a laminar structure is obtained.

In FIG. 2, reference numberal 32 designates a potentiometer for measuring an electromotive force which is induced between the reference electrode 10 and the measuring electrode 12, based on a difference in oxygen concentration between the reference gas and the measurement gas. Electric power from DC power source 32 is applied to the heating portion 30 to cause the heating element 26 to generate heat, and thereby heat a detecting portion of the electrochemical cell at which the electrodes 10, 12 are disposed, so that the sensing portion is maintained at a predetermined elevated operating temperature.

In the thus constructed and co-fired electrochemical oxygen sensing element of laminar structure, the conventionally experienced inconvenience of warpage arising from firing shrinkage is effectively restrained by the provision of the ceramic layers 18, 20 having the same firing shrinkage properties which are provided on both sides of the solid electrolyte body 2, 4, 6 which forms the electrochemical cell. Moreover, the provision of the planar electrical heater 22 permits the detecting portion of the cell to be held at its operating temperature, thereby improving the response characteristics of the cell.

Furthermore, the gas-tight ceramic structure 24, 24 in which the heating element 26 and leads 28, 28 are embedded, serves to effectively prevent the metal component (e.g., platinum) of the heating portion 30 from scattering at an elevated temperature, and protect the heating portion 30 against exposure to hot exhaust gas, whereby the possibility of electrical disconnection of the heating element 26 or leads 28, 28 is eliminated. Hence, the service life of the heater 22, and consequently the oxygen sensing element, may be prolonged.

In the instant arrangement, the electrical heater 22 is co-fired as an integral part of the electrochemical cell, with the porous ceramic layer 20 interposed therebetween. Consequently, a difference in thermal expansion between the support layer 6 and the gas-tight ceramic layer 24 is absorbed by the porous structure of the ceramic layer 20 interposed between the layers 6 and 24, whereby flake-off or cracks of these layers 6, 20, 24 is avoided. Since the support layer 6 is made of zirconia ceramics, the difference in thermal expansion between the layers 6 and 24 may be minimized by using zirconia as a major components of the gas-tight ceramic layers 24. In other words, the use of zirconia ceramics for the ceramic layer 24 contributes to prevention of flake-off of those layers.

Moreover, the electrical insulating property of the porous ceramic layer 20 interposed between the electrical heater 22 and the electrochemical cell (more precisely, support layer 6), blocks the flow of current which can leak from the heating portion 30 of the heater 22 toward the electrochemical cell, and obviates unfavourable influence of the leaked current upon the electromotive force of the electrochemical cell, which may lead to inaccurate or erroneous measurement of oxygen concentration of the measurement gas.

In order to attain effective heating of the detecting portion of the electrochemical cell, it is desired that the thickness of the porous ceramic layer 20 between the electrochemical cell and the electrical heater 22 be kept as small as possible to such extent that the ceramic layer 20 may serve as an electrical insulator for the heater 22. Generally, the thickness of the ceramic layer 20 should be held not greater than 300 microns, and particularly 10–200 microns.

Figure 3:
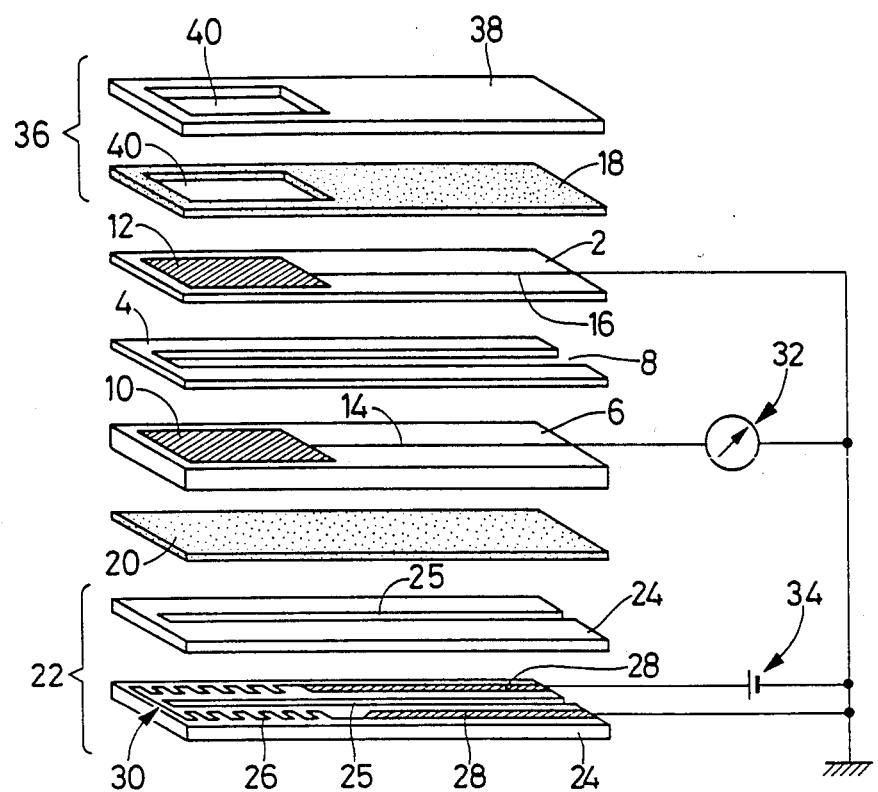

Referring next to FIG. 3, there is illustrated another form of an electrochemical sensing element, which is different from that of FIG. 2, in that an anti-warpage layer 36 is formed on the solid electrolyte layer 2 on which the measuring electrode 12 is disposed.

The anti-warpage layer 36 consists of a porous ceramic layer 18, and a ceramic layer 38 which is made of the same ceramic material as the gas-tight ceramic layers 24, 24. The anti-warpage layer 36 acts to prevent not only the warpage of the sensing element that would arise due to the interposition of the porous ceramic layer 20, but also the warpage that would be caused by the existence of the gas-tight ceramic layers 24 of the electrical heater 22. The porous ceramic layer 18 and the ceramic layer 38 of the anti-warpage layer 36 have rectangular openings 40 through which the measurement gas is introduced directly to the surface of the measuring electrode 12.

Figure 4:
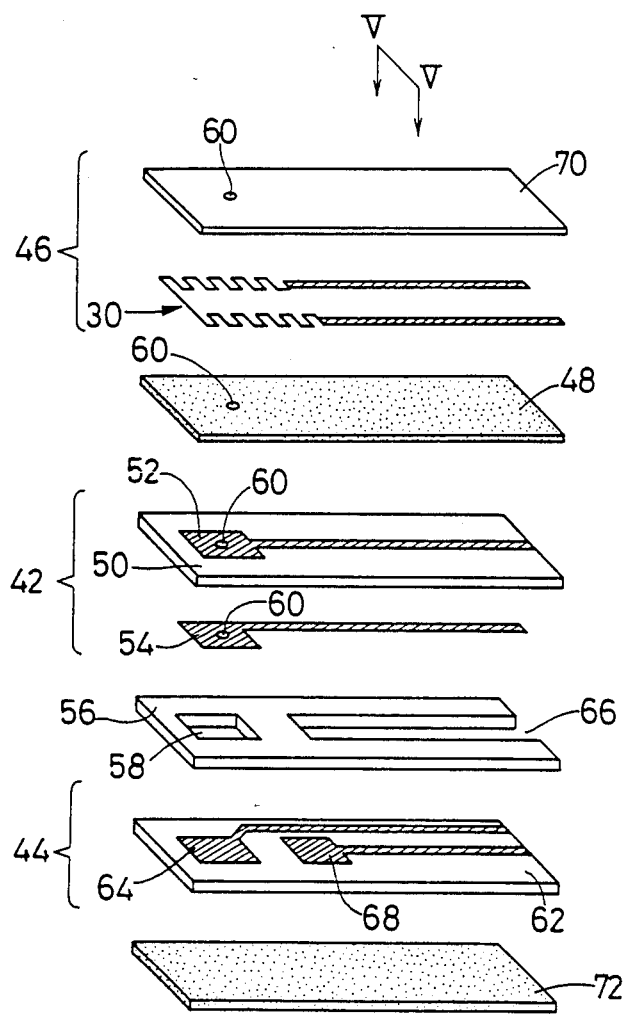
Figure 5:
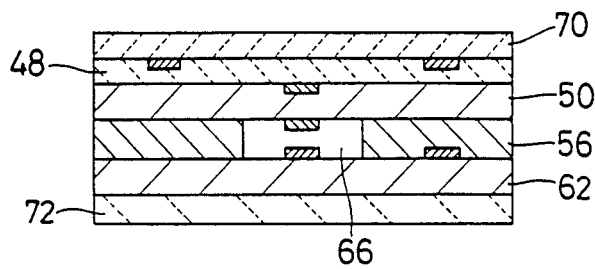
FIG. 5 is a schematic elevational view in cross section taken along line V—V of FIG. 4.

A further modified oxygen sensing element of the electrochemical device is depicted in FIGS. 4 and 5. This sensing element is suitably used as a lean-burn sensor for controlling an engine of the type which emits an exhaust gas of lean air-fuel ratios whose oxygen partial pressure is higher than that of the stoichiometric air-fuel ratio.

The oxygen sensing element of FIGS. 4 and 5 comprises an electrochemical cell assembly which includes two electrochemical cells, one of which is an oxygen pumping cell 42, and the other of which is an oxygen-concentration sensing cell 44. On the pumping cell 42, there is provided a planar electrical heater 46 similar to the heater 22 used in the preceding embodiment. A porous ceramic layer 48 is interposed between the electrical heater 46 and the pumping cell 42.

Described in greater detail, the pumping cell 42 includes a planar solid electrolyte layer 50 which carries, on its outer and inner surfaces, an outer pumping electrode 52 and an inner pumping electrode 54, respectively, such that the outer and inner electrodes 52, 54 are positioned in an aligned opposed relationship with each other. These pumping electrodes 52, 54 are connected to an external power source through respective electrical leads, to apply a predetermined voltage across the two pumping electrodes, so that oxygen in an amount proportional to the applied voltage is pumped in the direction of thickness of the solid electrolyte layer 50.

Between the pumping cell 42 and the sensing cell 44, there is disposed a spacer layer 56 which has a cavity 58. The measurement gas, such as an exhaust gas, is introduced into the cavity 58 through apertures 60 which are formed through the electrical heater 46, porous ceramic layer 48, and pumping cell 42. The apertures 60 have a small diameter selected to provide a predetermined diffusion resistance. With the operation of the pumping cell 42, the amount of a selected component of the measurement gas, (i.e., the amount of oxygen) to be introduced into the cavity 58 through the apertures 60 is controlled.

The oxygen-concentration sensing cell 44, which is similar in construction to the pumping cell 42, includes a planar solid electrolyte layer 62, a measuring electrode 64 exposed to the measurement gas in the cavity 58, and a reference electrode 68 exposed to the reference gas in a reference-gas passage 66 formed in the spacer layer 56. The thus constructed electrochemical sensing cell 44 serves as an oxygen concentration cell. The measuring and reference electrodes 64, 68 are electrically connected through respective electrical leads to an external measuring device to measure an electric potential difference between the electrodes 64, 68. Stated differently, the sensing cell 44 measures an electromotive force between the measuring electrode 64 exposed to the measurement gas in the cavity 58 in the spacer layer 56, and the reference electrode 68 exposed to the reference gas, based on a difference in oxygen concentration between the measurement gas and the reference gas.

The electrical heater 46 includes a ceramic gas-tight outermost layer 70 which covers the heating portion 30 and protects the same against exposure to the external measurement gas.

As previously indicated, the porous ceramic layer 48 is interposed between the electrical heater 46 and the oxygen pumping cell 42. The outer surface of the sensing cell 44 is covered by a porous ceramic layer 72 which is made of ceramics having substantially the same firing shrinkage property as the porous ceramic layer 48.

In the electrochemical sensing element constructed as described above, the electrically insulating porous ceramic layer 48 disposed between the heater 46 and the electrochemical pumping cell 42 is effective to prevent flake-off of these members, and leakage current from the heater 46. Further, the gas-tight ceramic outermost layer 70 of the heater 46 serves as an effective protector for the heating portion 30, that is, protects the same against deterioration due to exposure to the measurement gas, thereby considerably improving the durability of the electrical heater 46.

The porous ceramic layer 72 disposed on the outer side of the sensing cell 44 cooperates with the porous ceramic layer 48 made of the same material, to avoid otherwise possible warpage or buckling of the sensing element due to concurrent firing of the pumping cell 42, spacer layer 56, sensing cell 44 and electrical heater 46. Namely, the electrochemical cell assembly 42, 44 is sandwiched on its opposite sides by the porous ceramic layers 48, 72. According to this arrangement, a stress to cause warpage on the side of the porous ceramic layer 48 counteracts a stress to cause warpage on the side of the porous ceramic layer 72, whereby the possibility of warpage of the sensing element as a whole is substantially removed.

Figure 7:
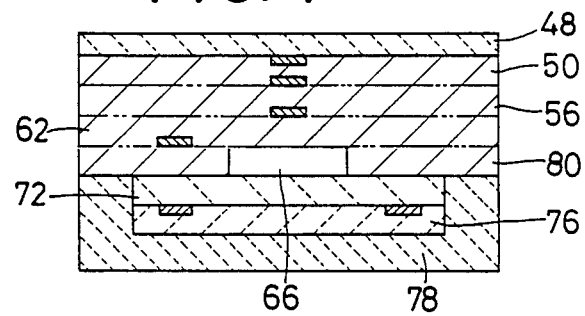
FIG. 7 is a schematic elevational view in cross section taken along line VII—VII of FIG. 6.
Figure 6:
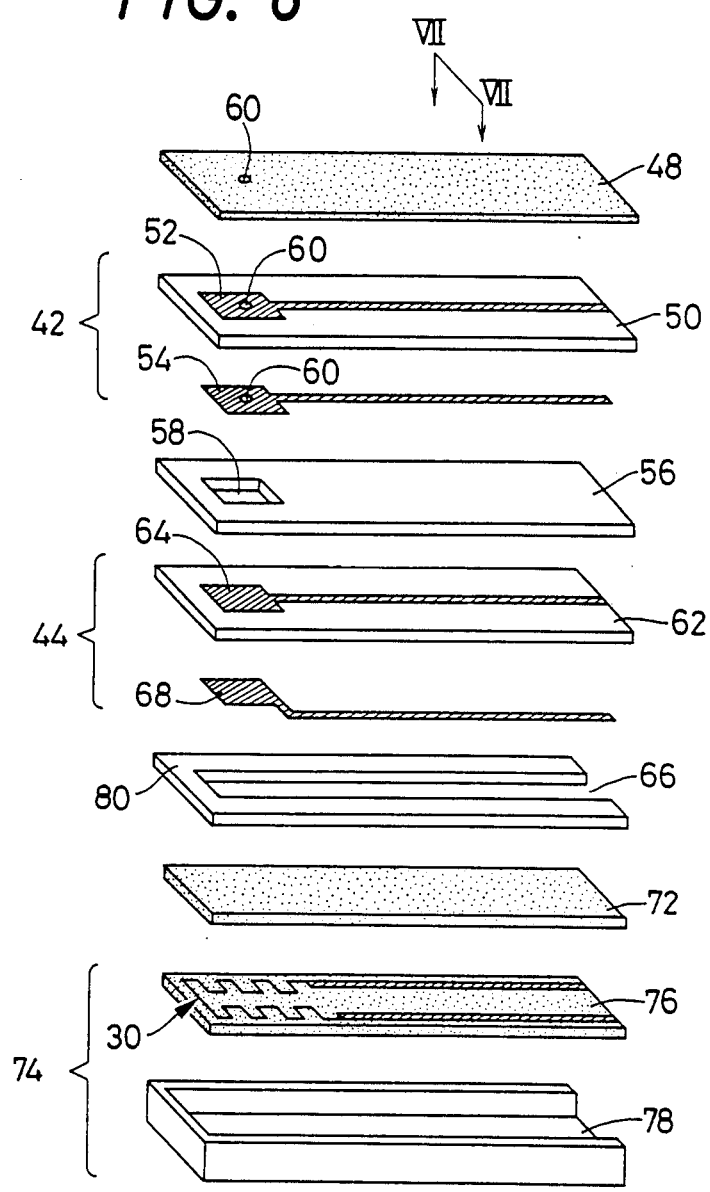
FIG. 6 is an exploded perspective view of another form of a sensing element of the electrochemical device.

Another modified form of an oxygen sensing element is shown in FIGS. 6 and 7, which is used as a lean-burn sensor similar to that of FIGS. 4 and 5. Unlike the sensing element of FIGS. 4 and 5, however, this modified sensing element has an electrical heater 74 on the outer side of the sensing cell 44, such that the porous ceramic layer 72 is interposed between the heater 74 and the sensing cell 44.

Described more specifically, the heating portion 30 of the electrical heater 74 is disposed on a ceramic support layer 76 of a porous structure, and embedded in a laminar porous ceramic structure 72, 76. The laminar porous ceramic structure 72, 76 is covered at its outer surface by a gas-tight ceramic outermost layer 78 and therefore protected against exposure to the external atmosphere. The thus constructed electrical heater 74 is co-fired together with the sensing cell 44, the porous ceramic layer 72, and a spacer layer 80 which has the reference-gas passage 66 and which is located on the side of the sensing cell 44 on which the reference electrode 68 is disposed.

In the oxygen sensing element described above, the two porous ceramic layers 48, 72 provided on opposite sides of the cell assembly, which consists of the pumping and sensing cells 42, 44, effectively prevent otherwise possible warpage of the sensing element. Furthermore, the interposition of the porous ceramic layer 72 between the sensing cell 44 and the electrical heater 74 provides a suitable solution to elimination of the flake-off trouble due to thermal expansion difference, and of the current leakage trouble. Moreover, the porous ceramic structure 72, 76 in which the heating portion 30 is embedded, is completely blocked by the gas-tight ceramic layer 78 against exposure to the external measurement gas. That is, the gas-tight ceramic layer 78 protects the heating portion 30 against deterioration due to exposure to the measurement gas.

Figure 9:
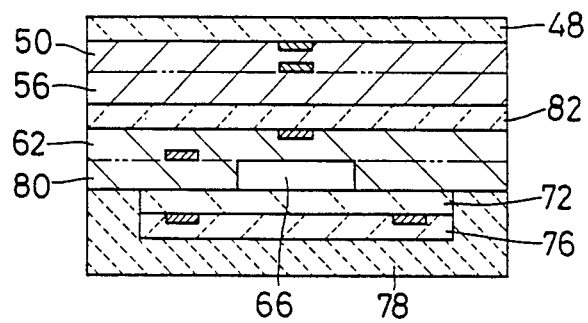
FIG. 9 is a schematic elevational view in cross section taken along line IX—IX of FIG. 8.
Figure 8:
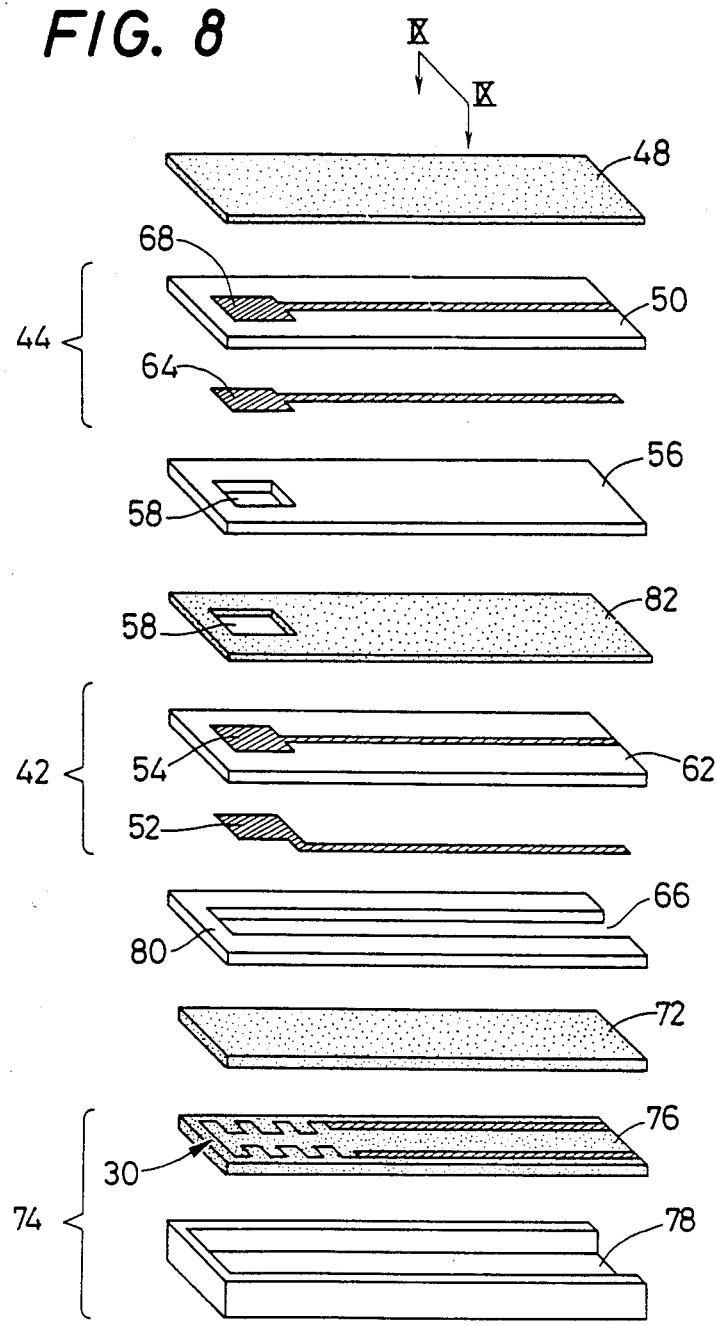
FIG. 8 is an exploded perspective view of a further form of a sensing element of the electrochemical device.

There is also illustrated in FIGS. 8 and 9 an oxygen sensor in the form of a lean-burn sensor similar to that shown in FIGS. 6 and 7. This sensor is characterized by an additional porous ceramic layer 82 which is interposed between the pumping cell 42 and the sensing cell 44.

In the preceding embodiment, the electrochemical cell assembly 42, 44 is sandwiched by the two porous ceramic layers. In this embodiment of FIGS. 8 and 9, each of the pumping and sensing cells 42, 44 is sandwiched on its opposite sides by two porous ceramic layers. That is, the porous ceramic layers 72 and 82 are disposed on the opposite sides of the oxygen pumping cell 42, respectively, to prevent warpage of the pumping cell 42. At the same time, the porous ceramic layers 82 and 48 are disposed on opposite sides of the oxygen sensing cell 44, respectively, to prevent warpage of the sensing cell 44. Thus, the warpage of the sensor as a whole is effectively avoided.

While the several preferred forms of the electrochemical sensing element constructed according to the invention have been described, the materials previously indicated for use in connection with the embodiment of FIG. 1 may be used in the modified embodiments of FIGS. 2-9 for the solid electrolyte layers (50, 56, 62, etc.), porous ceramic layers (48, 72, 76, 82), gas-tight ceramic layers (70, 78), electrodes (52, 54, 64, 68) and their electrical leads. By using the suitably selected materials, unfired laminar structures of the individual sensing elements are prepared in a known lamination or screen-printing process, and the prepared unfired laminar structures are co-fired into the integral planar sensing elements which are used in an electrochemical device.

It will be understood that the invention is by no means confined to the details of the illustrated embodiments, but may be otherwise embodied with various changes, modifications and improvements that may occur to those skilled in the art, without departing from the spirit of the invention.

For example, it is possible that two electrical heaters be provided on both sides of an electrochemical cell, rather than a single heater is provided on one side of the cell as in the illustrated embodiments.

While the electrical heater 22, 46, 74 may be energized by either AC or DC current, the arrangement according to the concept of the invention is advantageous particularly for obviating a problem of current leakage where a DC power supply is used for the electrical heater.

Although the illustrated electrochemical sensing elements according to the invention are suitably used as oxygen sensors, the invention may be embodied as other types of sensors or controllers for determining or controlling the concentration of specific components of a fluid associated with electrode reaction, other than oxygen such as nitrogen, carbon dioxide and hydrogen.

A few examples are given to further illustrate the preferred methods of preparing the products of this invention.

EXAMPLE 1

100 parts by weight of powder mixture consisting of 97 mole % of $ZrO_2$ and 3 mole % of $Y_2O_3$ was mixed with 1 part by weight of clay as a sintering agent, 8 parts by weight of polyvinyl butyral resin as a binder, 5 parts by weight of dioctyl phthalate, 100 parts by weight of trichloroethylene as a solvent. The obtained mixture slurry was cast, in a conventional doctor-blading process, to form the three unfired layers 2, 4, 6 of solid electrolyte shown in FIG. 3 so that each layer has 0.6 mm thickness.

Successively, a paste for the electrodes 10, 12 was prepared by adding 8% by weight of ethyl cellulose and 40% by weight of butyl carbitol to a powder mixture which consists of 90% by weight of platinum and 10% by weight of $ZrO_2$. With the prepared paste, unfired layers of the reference and measuring electrodes 10, 12 were screen-printed on the corresponding surfaces of the unfired layers 2 and 6, respectively.

A a paste was prepared by adding 10% by weight of polyvinyl butyral resin, 5% by weight of dibutyl sebacate and 40% by weight of butyl carbitol to a powder mixture which consists of 98% by weight of $Al_2O_3$, 1.5% by weight of $SiO_2$ and 0.5% by weight of CaO. By using the obtained paste, the porous ceramic layer 20 of 30 microns was formed by screen-printing on the surface of the unfired support layer 6 opposite to the surface on which the reference electrode 10 was formed.

For the gas-tight ceramic layers 24 each having the slit 25, a paste was prepared by adding 8% by weight of polyvinyl butyral resin, 3% by weight of dibutyl sebacate and 40% by weight of butyl carbitol to a powder mixture which consists of 79 mole % of $ZrO_2$, 11 mole % of $Nb_2O_3$ and 10 mole % of $Y_2O_3$. For the heating element and leads of the heating portion 30, a paste was prepared by adding 8% by weight of ethyl cellulose and 40% by weight of butyl carbitol to a powder mixture which consists of 80% by weight of platinum and 20% by weight of $Al_2O_3$. By using these pastes, unfired layers of the electrical heater 22 was formed by screen-printing on the outer surface of the unfired ceramic layer 20, such that the heating portion 30 was embedded between the gas-tight ceramic layers 24 each of which has a high electrical resistance and a thickness of 70 microns.

On the outer surface of the solid electrolyte layer 2 on which the measuring electrode 12 is disposed, the unfired ceramic layer 18 was screen-printed by using the same paste as used for forming the porous ceramic layer 20. The unfired ceramic layer 38 was then screen-printed on the unfirmed ceramic layer 18, by using the same paste as used for the gas-tight ceramic layer 24.

In the above manner, an unfired laminar structure of 40 mm length and 10 mm width was obtained. This unfired structure was co-fired in the atmosphere at 1400° C. Thus, integral oxygen sensing elements (oxygen sensors) of 30 mm length and 7.5 mm width were produced.

The produced oxygen sensing elements exhibited as small as about 0.1 mm warpage over the entire length of 30 mm, that is, exhibited substantially no warpage.

Moreover, comparative oxygen sensing elements were produced, without the porous ceramic layer 18, according to a conventional method, for comparison with the above-identified sensing elements produced according to the invention. These comparative sensing elements demonstrated an average warpage of 2 mm over their 30 mm length, such that the electrical heater was convexed outwardly.

EXAMPLE 2

With the method as used in Example 1, the five unfired layers 2, 4, 6, 24, 24 of solid electrolyte were formed, and unfired layers of the electrodes 10, 12 and heating portion 30 were formed by screen-printing on the appropriate layers 2, 4 and 24, respectively.

A paste was prepared by adding 10 parts by weight of polyvinyl butyral resin, 5 parts by weight of dioctyl phthalate, and 100 parts by weight of trichloroethylene (as a solvent) to 100 parts by weight of powder mixture which consists of 98% by weight of $MgO \cdot Al_2O_3$, 1.5% by weight of $SiO_2$ and 0.5% by weight of CaO. The obtained mixture slurry was cast, in a conventional doctor-blading process, to form the planar unfired ceramic layers 18 and 20 of FIG. 2 such that they have 0.1 mm thickness.

The thus prepared unfired layers 2, 4, 6, 24, 24 of solid electrolyte and ceramic layers 18, 20 were stacked on each other in the order shown in FIG. 2, and compacted at 80° C. with a pressure of 20 Kg/cm$^2$. As a result, an unfired laminar structure of 40 mm length and 10 mm width was obtained. The obtained unfired structure was then co-fired in the atmosphere at 1400° C. In this manner, the oxygen sensing elements of 30 mm length and 7.5 mm width were produced.

Like the oxygen sensing elements of EXAMPLE 1, the sensing elements of EXAMPLE 2 exhibited an average warpage of as little as 0.1 mm over the entire length of 30 mm, namely, substantially no warpage.

What is claimed is:

1. A method of manufacturing an electrochemical device which has a planar electrochemical cell structure including a planar solid electrolyte body and at least two electrodes disposed in contact with the solid electrolyte body, the device also including a heating element, comprising the steps of:
   forming a first unfired ceramic layer on a first side of an unfired electrochemical cell structure, said first unfired ceramic layer being given a porous structure by firing thereof;
   forming a second unfired ceramic layer on a second side of said unfired electrochemical cell structure, such that said second unfired ceramic layer does not contact either of said at least two electrodes, said second unfired ceramic layer being made of an electrically insulating material and being given a porous structure by firing thereof, said second unfired ceramic layer cooperating with said first unfired ceramic layer to prevent warpage of the planar electrochemical cell during co-firing of the unfired structure and unfired layers of the electrochemical cell;
   forming an unfired heater layer for the heating element, said unfired heater layer being embedded in said second unfired ceramic layer;
   forming a gas-tight unfired ceramic layer on one of the opposite sides of the second unfired ceramic layer which is remote from said first unfired ceramic layer, said gas-tight layer protecting the heater layer from exposure to a gas to be analyzed using said device; and
   co-firing said unfired electrochemical cell structure, said first unfired ceramic layer, said second unfired ceramic layer, said unfired heater layer, and said gas-tight unfired ceramic layer to form said electrochemical device.

2. A method as set forth in claim 1, wherein said first unfired ceramic layer is fired into a porous structure having a porosity within a range of 5-30%.

3. A method as set forth in claim 1, wherein the porous structure obtained by firing of said second unfired ceramic layer has a porosity within a range of 5-30%.

4. A method as set forth in claim 1, wherein said electrochemical cell structure includes a pumping cell and a sensing cell, said first unfired ceramic layer being formed so as to cover one side of an unfired structure of said pumping cell, said second unfired ceramic layer being formed so as to cover one side of an unfired structure of said sensing cell remote from the unfired structure of said pumping cell.

5. A method as set forth in claim 4, further comprising a step of forming a third unfired ceramic layer between said unfired structures of the pumping and sensing cells.

6. A method of manufacturing an electrochemical device which has a planar electrochemical cell structure including a planar solid electrolyte body and at least two electrodes disposed in contact with the solid electrolyte body, the device also including a heating element, comprising the steps of:
   forming a first unfired ceramic layer on one side of an unfired electrochemical cell structure, said first unfired ceramic layer being given a porous structure by firing thereof;
   forming a second unfired ceramic layer on the other side of said unfired electrochemical cell structure, such that said second unfired ceramic layer does not contact either of said at least two electrodes, said second unfired ceramic layer being made of an electrically insulating material and being given a porous structure by firing thereof;
   forming an unfired heater layer for the heating element, said unfired heater layer being embedded in said second unfired ceramic layer;
   forming a gas-tight unfired ceramic layer on one of the opposite sides of the second unfired ceramic layer which is remote from said first unfired ceramic layer, said gas-tight layer protecting the heater layer from exposure to a gas to be analyzed using said device; and
   co-firing said unfired electrochemical cell structure, said first unfired ceramic layer, said second unfired ceramic layer, said unfired heater layer, and said gas-tight unfired ceramic layer to form said electrochemical device.

7. A method as set forth in claim 6, wherein said first unfired ceramic layer is fired into a porous structure having a porosity within a range of 5-30%.

8. A method as set forth in claim 6, wherein the porous structure obtained by firing of said second unfired ceramic layer has a porosity within a range of 5-30%.

9. A method as set forth in claim 6, wherein said electrochemical cell structure includes a pumping cell and a sensing cell, said first unfired ceramic layer being formed so as to cover one side of an unfired structure of said pumping cell, said second unfired ceramic layer being formed so as to cover one side of an unfired structure of said sensing cell remote from the unfired structure of said pumping cell.

10. A method as set forth in claim 9, further comprising a step of forming a third unfired ceramic layer between said unfired structures of the pumping and sensing cells .

* * * * *